(12) United States Patent
Williams

(10) Patent No.: US 8,413,658 B2
(45) Date of Patent: Apr. 9, 2013

(54) ORAL AIRWAY FOR ENDOSCOPIC AND INTUBATING PROCEDURES

(76) Inventor: Andrea R. Williams, Hanover, NH (US)

(*) Notice: Subject to any disclaimer, the term of this patent is extended or adjusted under 35 U.S.C. 154(b) by 1140 days.

(21) Appl. No.: 12/131,435

(22) Filed: Jun. 2, 2008

(65) Prior Publication Data

US 2009/0013995 A1    Jan. 15, 2009

Related U.S. Application Data

(63) Continuation-in-part of application No. 11/838,975, filed on Aug. 15, 2007, now abandoned.

(60) Provisional application No. 60/851,506, filed on Oct. 13, 2006.

(51) Int. Cl.
*A61M 16/00* (2006.01)

(52) U.S. Cl.
USPC .................................. 128/207.14; 128/200.26

(58) Field of Classification Search ............. 128/200.26, 128/204.18, 207.14–207.17, 207.12, 207.13
See application file for complete search history.

(56) References Cited

U.S. PATENT DOCUMENTS

| | | | | |
|---|---|---|---|---|
| 1,498,810 A * | 6/1924 | Poe | ........... | 128/200.26 |
| 2,705,959 A * | 4/1955 | Elmore | ........... | 128/207.14 |
| 3,756,244 A * | 9/1973 | Kinnear et al. | ........... | 128/207.14 |
| 3,908,665 A * | 9/1975 | Moses | ........... | 128/207.14 |
| 4,198,970 A * | 4/1980 | Luomanen | ........... | 128/207.15 |
| 4,495,945 A * | 1/1985 | Liegner | ........... | 128/200.26 |
| 4,683,879 A * | 8/1987 | Williams | ........... | 128/200.26 |
| 5,174,283 A * | 12/1992 | Parker | ........... | 128/200.26 |
| 5,235,973 A * | 8/1993 | Levinson | ........... | 128/207.15 |
| 5,285,778 A * | 2/1994 | Mackin | ........... | 128/207.15 |
| 5,287,848 A * | 2/1994 | Cubb et al. | ........... | 128/200.26 |
| 5,291,882 A * | 3/1994 | Makhoul et al. | ........... | 128/207.14 |
| 5,445,161 A * | 8/1995 | Huang | ........... | 600/532 |
| 5,582,167 A * | 12/1996 | Joseph | ........... | 128/207.15 |
| 5,791,341 A * | 8/1998 | Bullard | ........... | 128/207.15 |
| 5,937,858 A | 8/1999 | Connell | | |
| 6,098,617 A | 8/2000 | Connell | | |
| 6,116,284 A * | 9/2000 | Murray et al. | ........... | 138/39 |
| 6,474,332 B2 * | 11/2002 | Arndt | ........... | 128/200.26 |
| 6,550,475 B1 * | 4/2003 | Oldfield | ........... | 128/200.26 |
| 6,631,720 B1 * | 10/2003 | Brain | ........... | 128/207.14 |
| 6,843,250 B2 * | 1/2005 | Efrati | ........... | 128/207.14 |
| 7,013,899 B2 * | 3/2006 | Alfery et al. | ........... | 128/207.18 |
| 7,036,501 B2 * | 5/2006 | Wall | ........... | 128/200.26 |
| 7,171,962 B1 * | 2/2007 | Bloem | ........... | 128/200.26 |
| 7,273,050 B2 * | 9/2007 | Wei | ........... | 128/200.26 |
| 7,278,420 B2 | 10/2007 | Ganesh et al. | | |
| 7,360,541 B2 * | 4/2008 | Dhuper et al. | ........... | 128/207.14 |
| 7,503,328 B2 * | 3/2009 | Kolobow et al. | ........... | 128/207.14 |
| 7,913,687 B2 * | 3/2011 | Munn | ........... | 128/200.26 |

(Continued)

*Primary Examiner* — Lynne Anderson
*Assistant Examiner* — Bradley Philips
(74) *Attorney, Agent, or Firm* — Michael Diaz

(57) ABSTRACT

An oral airway providing a patent airway to a patient, supplies oxygen to the patient and monitors expelled gases during endoscopic or intubating procedures. The oral airway includes a central lumen and two lateral breathing channels. A bracket at the proximal end of the oral airway functions to guide an oxygen supply line and an end tidal carbon dioxide monitoring line into the lateral breathing channels and to act as a barrier beyond which the airway cannot be inserted into the mouth of the patient. The airway has a straight main central lumen which serves as a guide and conduit to facilitate endoscope, bronchoscope, or fiber optic bronchoscope placement and manipulation.

19 Claims, 4 Drawing Sheets

U.S. PATENT DOCUMENTS

| | | | |
|---|---|---|---|
| 7,934,502 B2 * | 5/2011 | Cook | 128/207.15 |
| 7,946,289 B2 * | 5/2011 | Munn | 128/200.26 |
| 7,954,488 B2 * | 6/2011 | Munn | 128/200.26 |
| 2002/0014238 A1 * | 2/2002 | Kotmel | 128/204.18 |
| 2003/0051733 A1 * | 3/2003 | Kotmel et al. | 128/207.14 |
| 2004/0020491 A1 * | 2/2004 | Fortuna | 128/207.15 |
| 2004/0123867 A1 * | 7/2004 | Efrati | 128/207.14 |
| 2004/0129272 A1 * | 7/2004 | Ganesh et al. | 128/207.14 |
| 2006/0032505 A1 * | 2/2006 | Alfery et al. | 128/207.14 |
| 2006/0180156 A1 * | 8/2006 | Baska | 128/207.15 |
| 2006/0272647 A1 | 12/2006 | Hauge | |
| 2007/0006878 A1 * | 1/2007 | Mackey et al. | 128/200.26 |
| 2008/0000481 A1 * | 1/2008 | Ganesh et al. | 128/207.14 |
| 2008/0216839 A1 * | 9/2008 | Rutter | 128/207.14 |
| 2009/0038620 A1 * | 2/2009 | Efrati | 128/207.14 |
| 2009/0101140 A1 * | 4/2009 | Miller et al. | 128/200.26 |
| 2010/0101567 A1 * | 4/2010 | Hauge | 128/200.26 |
| 2011/0265800 A1 * | 11/2011 | Baska | 128/207.15 |
| 2012/0000471 A1 * | 1/2012 | Harrington et al. | 128/207.15 |
| 2012/0048278 A1 * | 3/2012 | Yasick | 128/207.14 |

* cited by examiner

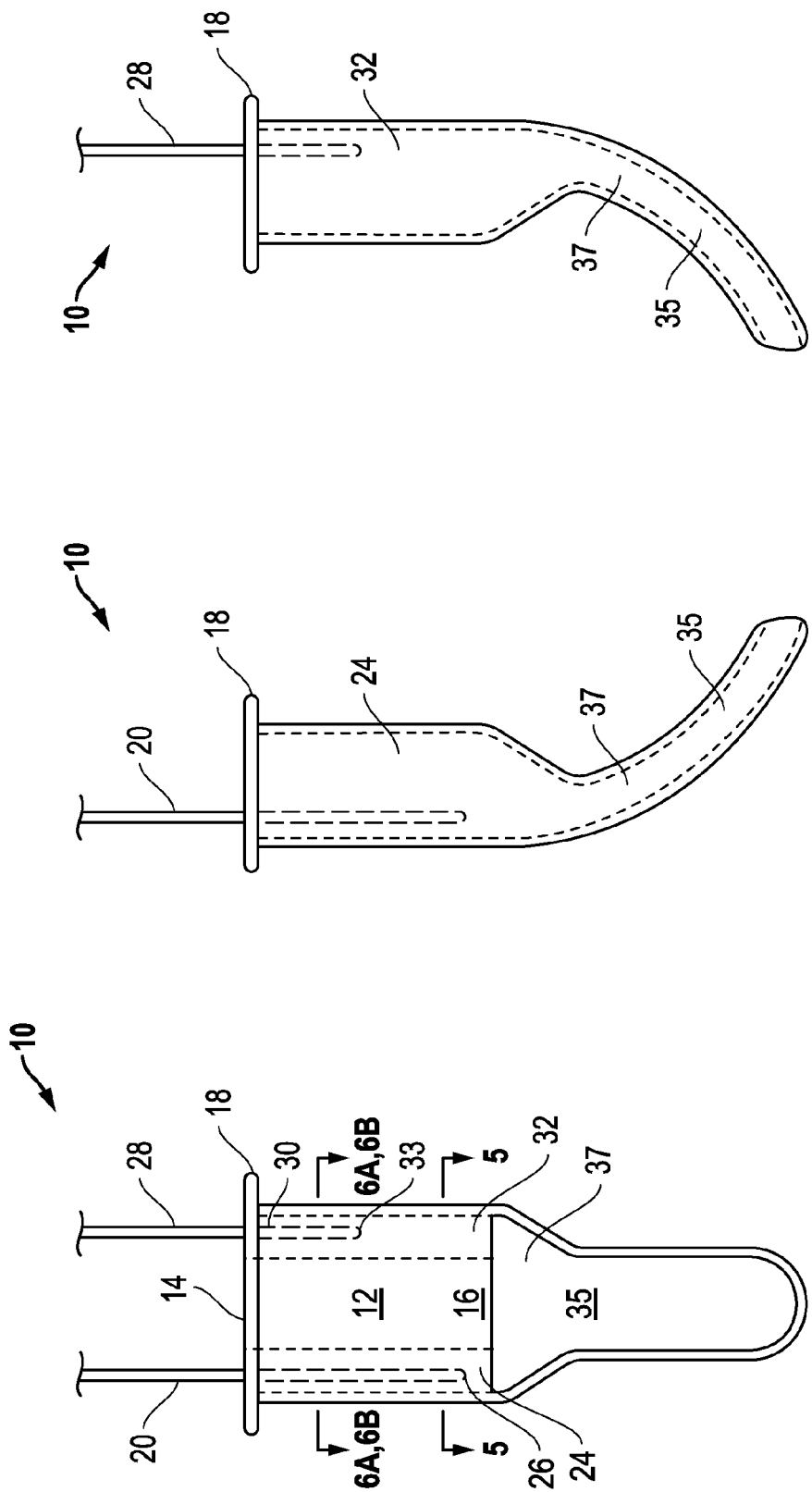

ORAL AIRWAY FOR ENDOSCOPIC AND INTUBATING PROCEDURES

RELATED APPLICATIONS

This application is a continuation-in-part application of U.S. patent application Ser. No. 11/838,975 entitled "ORAL CANNULA AIRWAY" filed on Aug. 15, 2007 now abandoned under the name of Andrea R. Williams which claims the priority date of Provisional Patent Application No. 60/851,506 filed Oct. 13, 2006 and is hereby incorporated by reference.

BACKGROUND OF THE INVENTION

1. Field of the Invention

This invention relates to medical devices. Specifically, the present invention relates to an oral airway for maintaining a patent airway for spontaneously ventilating patients undergoing sedation for surgical, endoscopic, bronchoscopic, and fiber optic intubation procedures.

2. Description of the Related Art

Each year in the United States, more than twenty million surgeries are performed on an outpatient basis. With these surgeries, as well as those performed in office-based surgical practices, regional/local anesthesia and intravenous sedation are growing in popularity as the preferred sedation method. Nurses having little or no specialized anesthesia training are administering intravenous sedation for a growing number of procedures. Compared to general anesthesia, patients can recover more quickly and experience less postoperative pain and nausea and vomiting, while experiencing greater satisfaction and more rapid discharge to their homes.

Airway emergencies are the most common complication during moderate and deep procedural sedation. One of the earliest indications of airway compromise is a change in end tidal carbon dioxide ($ETCO_2$). Currently, there are several options to manage the airway of sedated patients: oral endotracheal tubes (OETT); the laryngeal mask airway (LMA); and the cuffed oral pharyngeal airway (COPA). All of these options require advanced training and connection of the device to some external form of supplemental oxygen or an anesthesia circuit, and are not available to the non-anesthesia trained nurse.

As discussed in co-pending U.S. patent application Ser. No. 11/838,975, a nasal oxygen cannula is typically used to supplement oxygen in patients under sedation who are able to maintain an unobstructed airway, and is frequently accompanied by $ETCO_2$ monitoring. The nasal oxygen cannula is not, however, capable of assisting the patient in maintaining a clear airway. Since patients under sedation often experience relaxed oral or pharyngeal tissues which may interfere with breathing, additional mechanical assistance may be required to maintain a patent airway in these circumstances. Additionally, sedated patients undergoing procedures through the mouth, such as endoscopy and bronchoscopy, frequently experience airway obstruction. Although OETT, LMA and COPA provide this mechanical assistance, they are poorly tolerated by patients unless deep sedation or general anesthesia is administered.

Although there are no known prior art teachings of a solution to the aforementioned deficiency and shortcoming such as that disclosed herein, prior art references that discuss subject matter that bears some relation to matters discussed herein are U.S. Pat. No. 7,278,420 to Ganesh et al. (Ganesh), U.S. Pat. No. 4,683,879 to Williams (Williams), and U.S. Pat. No. 6,098,617 to Connell (Connell).

Ganesh discloses an oropharyngeal device for insertion into the mouth of a patient. The device includes a distal end and proximal end having a flange formed at the proximal end. The body is sized such that the distal end of the body is disposed within the pharynx above the epiglottis. The device includes at least three separate conduits integrated into the body for administering oxygen, suctioning and for assessing ventilation through end-tidal carbon dioxide monitoring. However, Ganesh does not disclose a device for use in maintaining an airway during endoscopic or intubating procedures. Furthermore, Ganesh suffers from the disadvantage of placing the end-tidal carbon dioxide monitoring conduit near the proximal end of the device, which is not the most advantageous position to obtain accurate readings from the patient.

Williams discloses a dual function connector for releasable attachment to an endopharyngeal tube or airway intubator. However, Williams does not teach or suggest a device for maintaining an airway, providing oxygen supplementation, or $ETCO_2$ monitoring for a patient.

Connell discloses a device adapted for use with a conventional oral or nasopharyngeal airway for delivering an inhalant gas to a proximal end of the airway and for sampling exhalent gas at a distal end of the airway. However, Connell does not teach or suggest a device for use in maintaining an airway during an endoscopic or intubating procedure.

It would be an advantage to have a device which maintains a patent airway, provides for oxygen supplementation and $ETCO_2$ monitoring in spontaneously ventilating, sedated patients as well as allows the placement and use of scopes in various medical procedures. Furthermore, a device is needed which enables the airway device to be used by non-anesthesia trained medical providers. It is an object of the present invention to provide such an apparatus.

SUMMARY OF THE INVENTION

In one aspect, the present invention is directed to an oral airway. The airway includes a main central lumen having a proximal end and an opposite distal end. The main central lumen contains an enlarged straight hollow oral airway which is large enough to accommodate and manipulate an endoscope or bronchoscope. The oral airway includes two lateral breathing channels located on opposite sides of the main lumen. Oxygen and ETCO2 are supplemented and monitored respectively through the lateral breathing channels. At the proximal end of the oral airway, a bracket guides and secures an $ETCO_2$ line and an $O_2$ line into the interior of the airway. The bracket also acts as a barrier, beyond which the airway cannot be inserted into the mouth of a patient. On the proximal side of the bracket, the $ETCO_2$ line and the $O_2$ line extend to an $ETCO_2$ monitor and an oxygen supply, respectively. On the distal side of the bracket, the $O_2$ line enters and extends into the proximal third of one of the breathing channels, allowing for supplemental oxygen to be supplied to the oral airway. Also on the other distal side of the bracket, the $ETCO_2$ line enters the other lateral breathing channel and extends through the oral airway to the middle third of the breathing channel, allowing carbon dioxide sampling as expelled gases from a patient enters the distal end of the lumen.

In another aspect, the present invention is directed to an oral airway system. The oral airway includes a main central airway lumen having a straight passageway allowing accommodation of endoscopes and bronchoscopes. The main central airway lumen has a proximal end and an opposite distal end. The oral airway also includes a gas supply line located in a first breathing channel adjacent to the airway lumen. Additionally, the oral airway includes a gas monitoring line located in a second breathing channel adjacent to the airway lumen for monitoring gases expelled from a patient. A gas monitoring system is connected to the gas monitoring line. The oral airway system also includes a gas supply system connected to the gas supply line. The oral airway is inserted into the mouth of the patient so that the distal end is placed in the patient's pharynx and the proximal end remains outside the mouth of the patient. The gases expelled by the patient are sent through the gas monitoring line to the gas monitoring system. The gas supply system supplies gas through the gas supply line to the patient.

BRIEF DESCRIPTION OF THE DRAWINGS

FIG. 2 is a front interior view of the main airway lumen of FIG. 1;

FIG. 3 is a right side view of the main airway lumen;

FIG. 4 is a left side view of the main airway lumen;

DESCRIPTION OF THE INVENTION

Figure 1:
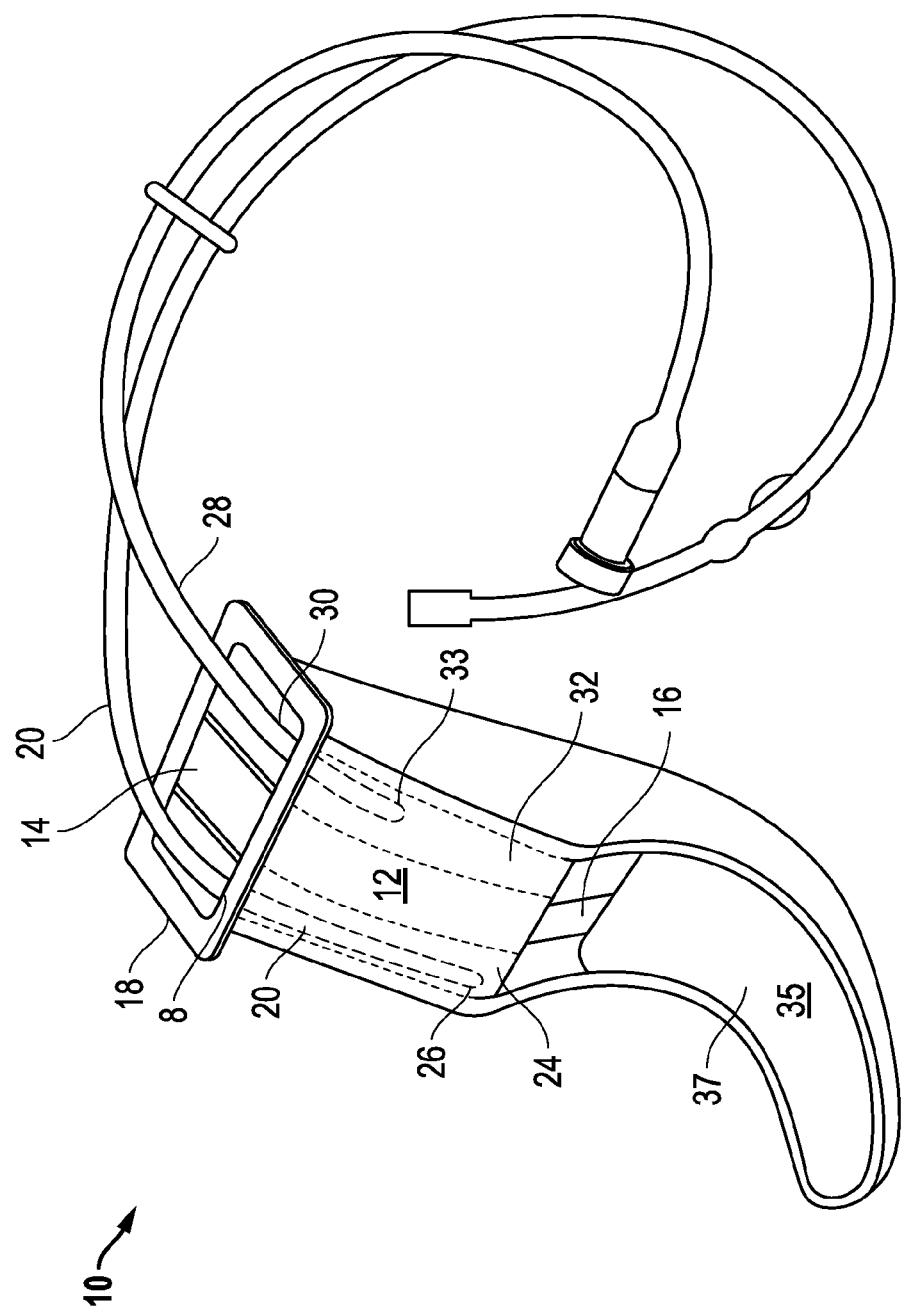
FIG. 1 is a front perspective view of an oral airway in the preferred embodiment of the present invention.

An oral airway for use in spontaneously ventilating patients during endoscopic or intubating procedures is disclosed. FIG. 1 is a front perspective view of an oral airway 10 for use in endoscopic or intubating procedures in the preferred embodiment of the present invention. The oral airway includes a substantially central and straight working channel or airway lumen 12 sized and shaped to accommodate an endoscope or bronchoscope. The airway lumen 12 includes at least two adjacent lateral, curved breathing channels 24 and 32. The oral airway 10 includes the main airway lumen 12 having a proximal end 14 and a distal end 16. The lumen 12 is preferably straight for ease in maneuvering and turning scopes within and distal to the lumen as the scopes exit the distal lumen without obstruction or limitation of movement, which may occur with a curved lumen shape. A bracket 18 is preferably secured to the proximal end 14 of the airway lumen 12. An $ETCO_2$ line 20 is positioned through the bracket 18 and enters the lateral breathing channel 24 at an entry point 8. The $ETCO_2$ 20 line preferably extends into the curved lateral breathing channel 24 to an endpoint 26 located in the middle third of the lateral breathing channel 24. The curved lateral breathing channel 24 preferably extends past the endpoint 26. In addition, an oxygen ($O_2$) line 28 is positioned through the bracket 18 and enters the opposite lateral breathing channel 32 at an entry point 30. The O2 line preferably extends into the proximal third of the airway and ends at endpoint 33. The curved lateral breathing channel 32 continues past 33. In addition, to securing the ETCO2 line 20 and O2 line 28, the bracket 18 prevents insertion of the entire airway lumen into the mouth of the patient. The oral airway 10 also includes an extension 35 providing a curved extension with a partially opened portion 37 of the oral airway for scope manipulation and breathing channels to converge. The extension 35 is preferably shaped as a "scoop" which, when utilized in a patient, has the distal end of the extension positioned in the posterior pharynx, posterior and distal to the tongue and proximal to the epiglottis. The extension 35 is important to allow scope maneuvers without impingement by the oral airway itself.

Figure 5:
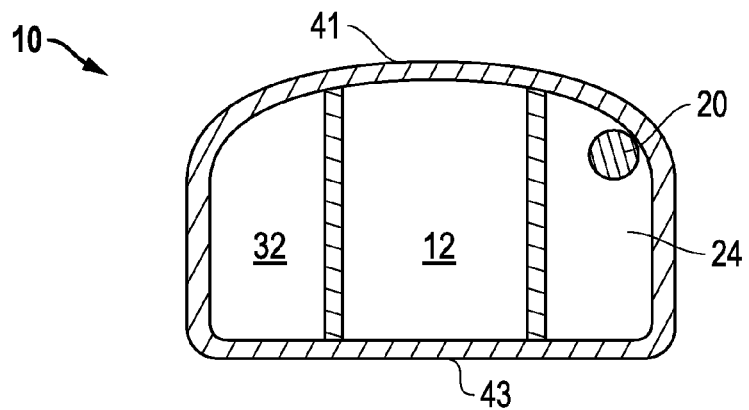
FIG. 5 is a cross section view of the main airway lumen midsection.

FIG. 2 is a front interior view of the oral airway 10 of FIG. 1. FIG. 3 is a right side view of the oral airway 10. FIG. 4 is a left side view of the oral airway 10. FIG. 5 is a cross section of the oral airway 10 at the midsection of the lumen 12. The oral airway 10 preferably has a curved portion 41 and a flat straight side 43, thereby providing a "half moon" shape cross section. The oral airway 10 includes the airway lumen 12 for accommodating endoscopes, bronchoscopes or other surgical instruments. The lateral breathing channel 24 is located adjacent to the airway lumen having the $ETCO_2$ line 20 within the interior of the lateral breathing channel 24. In addition, the lateral breathing channel 32 is located on an opposite side of the channel 24.

In the preferred embodiment of the present invention, the $O_2$ line 28 enters the lateral breathing channel at the proximal end and includes an entry point into the passageway of the lateral airway breathing channel lumen extending approximately two centimeters into the lateral breathing channel. The channel preferably is 0.75 centimeters wide and approximately two centimeters in height. The $ETCO_2$ line 20 enters the opposite lateral breathing channel at the proximal end and preferably extends into the lateral breathing channel approximately four centimeters. The associated breathing channel is also preferably 0.75 centimeters wide with an approximate height of two centimeters. In the preferred embodiment of the present invention, the length of the oral airway is in the range of 8.0-10.0 centimeters for adults. For children, the oral airway may be smaller.

Figure 6A:
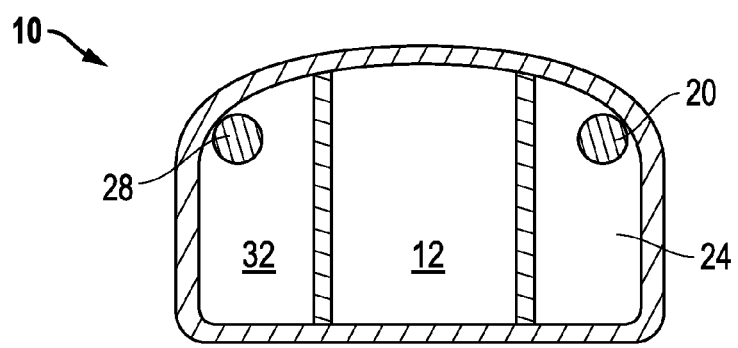
FIG. 6A illustrates a cross sectional view of the proximal oral airway in the preferred embodiment of the present invention.

FIG. 6A illustrates the cross sectional of the oral airway 10. As discussed above, the oral airway preferably has a half-moon shape which provides stability for the airway such that manipulation of scopes in the airway does not cause it to roll or turn in the patient's mouth. As shown in FIG. 6A, the breathing channels are separated from each other and the lumen 12. By separating the breathing channels, a more accurate sampling of ETCO2 may occur because of less dilution and distortion of the ETCO2 tracing from inspired oxygen.

Figure 6B:
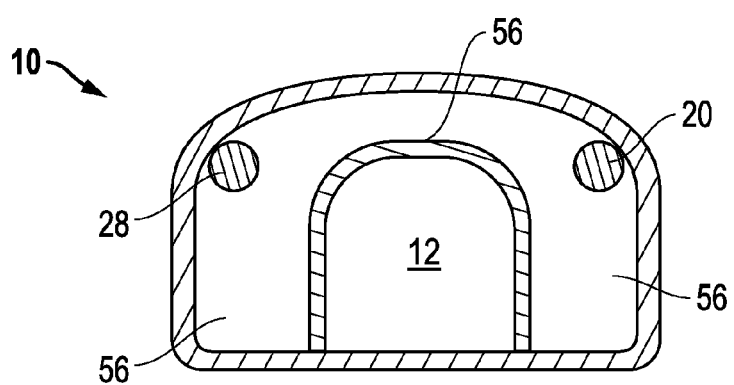
FIG. 6B illustrates a cross sectional view of the oral airway in an alternate embodiment of the present invention.

FIG. 6B illustrates a cross sectional view of the oral airway in an alternate embodiment of the present invention. A single breathing channel 56 may surround the lumen 12 and accommodate both the $O_2$ line 28 and the $ETCO_2$ line 20.

Figure 7:
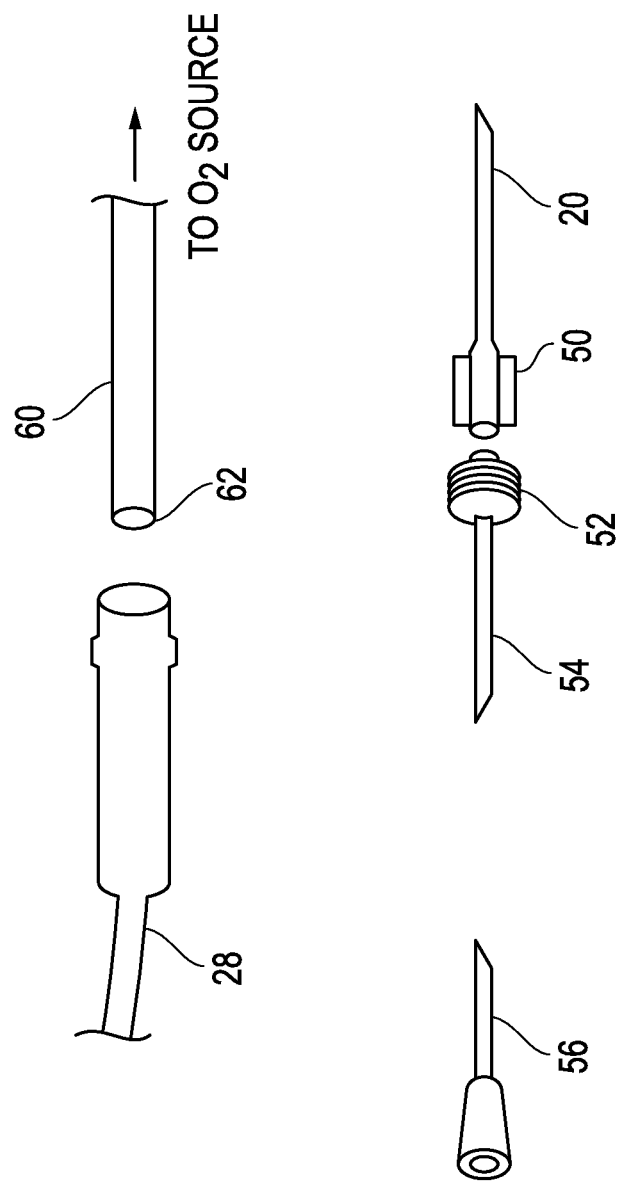
FIG. 7 is a side view of a connection arrangement of the $ETCO_2$ and $O_2$ lines.

FIG. 7 is a side view of a connection arrangement 40 of the $ETCO_2$ line 20 in the preferred embodiment of the present invention. Referring to FIGS. 1 and 7, the $ETCO_2$ line 20 extends from the bracket 18 to a female luer connector 50. The female luer connector may be connectable to a male luer 52. The male luer 52 is a standard connection to the $ETCO_2$ sample line connecting to the $ETCO_2$ monitor. Alternatively, the male luer may be secured to an adapter line 54 having an adapter female connector 56. A plain, thin $ETCO_2$ sample line without a male connector from the $ETCO_2$ monitor may be inserted into connector 56. The $O_2$ line 28 extends from the bracket 18 and may include a connector 60 located on an end 62. The $O_2$ line connector 60 attaches to the $O_2$ line which attaches to any standard "Christmas tree" connector to an $O_2$ source. The $O_2$ line and the $ETCO_2$ lines are preferably constructed of flexible plastic tubing common in medical devices.

In the preferred embodiment of the present invention, the $ETCO_2$ line is preferably located inside the middle third of the lateral breathing channel 24 (e.g., approximately 4 centimeters from the proximal end 8) to facilitate accurate measurement of the expired carbon dioxide. The $O_2$ line is preferably in the opposite lateral breathing channel 32, approximately two centimeters proximal to the $ETCO_2$ line. This location ensures delivery of oxygen to the lower oral pharyngeal airway with minimal interference in $ETCO_2$ tracing. The proximal ends of the sampling and delivery tubing are preferably connected to the $ETCO_2$ monitor and to any oxygen supply system via a double lumen oxygen delivery line with an $ETCO_2$ sampling channel. In addition, the lateral breathing channels are large enough for a separate suctioning line to pass if necessary.

The oral airway 10 maintains a patent airway as the firm non-traumatic distal end 35 creates a patent breathing channel which supports the relaxed soft tissues of the sedated patient and facilitates endoscope and bronchoscope use. The oxygen delivery system ($O_2$ line 28) utilized with the present invention may be directly connected to a wall or tank $O_2$, or the oxygen flow system of any standard anesthesia machine. The $ETCO_2$ line 20 may connect to any $ETCO_2$ monitoring system via a standard universal female/male luer connector. The present invention does not require connection to the ventilator/anesthesia circuit. If a patient requires assisted ventilation, this may be provided by bag/mask ventilation while still providing airway support, supplemental oxygen, and $ETCO_2$ monitoring.

With reference to FIGS. 1-7, the operation of the oral airway 10 will now be explained. The oral airway 10 may be used in conjunction with an ETCO2/O2 nasal cannula (not shown). In this case, sedation using normal procedures known to the art is commenced before a surgical or medical procedure, endoscopic or bronchoscopic exam, or fiber optic intubation. The nasal cannula is also placed using normal procedures known to the art. After adequate moderate to deep levels of sedation have been reached and the patient's glossopharyngeal reflexes have been suppressed, the distal end 35 is inserted into the patient's mouth so that the portion of the main airway lumen 12 which is not in the patient's mouth curves up in the direction of the patient's nose. As the main airway lumen 12 is advanced into the patient's mouth, it must be rotated 180 degrees as it passes into the pharynx. In the fully inserted position, the proximal end 14 is in the patient's mouth, except for the bracket 18 which prevents further advancement of the lumen. The bracket 18 remains outside the patient's lips, and the distal end is curved along the pharynx.

With the main airway lumen 12 in place, an $ETCO_2$ monitor line and an oxygen supply line (not shown) are disconnected from the nasal cannula and connected to the $ETCO_2$ line 20 and the $O_2$ line 28 in the respective lateral breathing channels 24 and 32.

Once the medical procedure is complete and the patient begins to awaken, the $ETCO_2$ line 20 and the $O_2$ line 28 are disconnected from the $ETCO_2$ monitor and $O_2$ supply, respectively, and reattached to the nasal cannula. The main airway lumen 12 may then be withdrawn by medical personnel or alternatively by action of the patient's tongue or mouth.

The oral airway 10, in the preferred embodiment of the current invention, may also be used without an accompanying nasal cannula. The $ETCO_2$ line 20 and the $O_2$ line 28 are connected to the $ETCO_2$ monitor and $O_2$ supply, respectively, before insertion of the main airway lumen 12. The distal end 35 of the main airway lumen 12 is inserted into the patient's mouth and held between the patient's lips with the remainder of the lumen curving up toward the patient's nose as above. As sedation of the patient begins and the glossopharyngeal reflexes have been suppressed, the main airway lumen 12 is advanced into the pharynx and rotated 180 degrees as the distal end 35 passes into the posterior pharynx. Following the medical procedure, when the patient begins to regain glossopharyngeal reflexes, the insertion procedure is reversed and the main airway lumen is withdrawn until only the distal end 35 remains in the patient's mouth. As the patient awakens and can respond to verbal instructions, the patient is asked to open his mouth and the main airway lumen 12 is fully removed.

In an alternate embodiment of the present invention, the main airway lumen 12 may not include a bracket. The proximal end 14 of the main airway lumen may be wider than the main body of the main airway lumen to prevent insertion of the entire main airway lumen 12 into the mouth of a patient. It should also be understood by those skilled in the art that the main airway lumen may be shaped in any fashion which allows the insertion of the oral cannula airway 10 into the patient's mouth. Additionally, the $ETCO_2$ line 20 and the $O_2$ line 28 may be positioned anywhere within the interior of the main airway lumen and still remain in the scope of the invention. The $ETCO_2$ line 20 may monitor expel gases other than carbon dioxide. In addition, the $O_2$ line 28 may provide gases other than oxygen to the patient.

The present invention provides many advantages over existing airway devices. The present invention provides a simple method to maintain an open airway, administer supplemental oxygen and monitor expired gases. It is ideal for maintaining a patent airway in spontaneously ventilating surgical patients undergoing procedures where local or regional anesthesia and moderate to deep sedation with sedative drugs are employed. It maintains a patent airway in spontaneously ventilating sedated patients undergoing endoscopy, bronchoscopy or fiber optic intubation. In addition, it may be used by providers not specially trained in anesthesia procedures for administering intravenous procedural sedation.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. An oral airway, the oral airway comprising:
   a central airway lumen having a passageway, the central airway lumen having a proximal end and an opposite distal end;
   a first breathing channel positioned adjacent to the central airway lumen, the first breathing channel having a gas supply line, the gas supply line adapted to supply gas from a gas supply device to the passageway; and
   a second breathing channel positioned adjacent to the central airway lumen and opposite the first breathing channel, the second breathing channel having a gas monitoring line for monitoring gases expelled from a patient, the gas monitoring line providing a conduit to monitor expelled gases within the passageway and adapted for connection to a gas monitor device;
   wherein the airway lumen is a unitary body having a curved extension with a partially opened portion of the oral airway for scope manipulation, the shape of the oral airway providing a patent airway for spontaneously ventilating patients undergoing moderate to deep sedation for surgical procedures, endoscopic procedures, bronchoscopic procedures, or fiber optic intubation;

wherein the airway lumen is sized and shaped to enable scope manipulation by inserting a scope through the proximal end and exiting the scope through the distal end;

whereby the central airway lumen is inserted into the mouth of a patient so that the distal end is positioned in the patient's pharynx and the proximal end remains outside the mouth of the patient and wherein the first breathing channel constantly supplies gas to the patient and the second breathing channel constantly monitors expelled gases from the patient while simultaneously enabling scope manipulation through the airway lumen.

2. The oral airway of claim 1 wherein:
the central airway lumen is straight; and
the first and second breathing channels and central lumen converge into a single curved partially opened distal extension.

3. The oral airway of claim 1 wherein the central lumen and two lateral breathing channels converge into a single distal common airway.

4. The oral airway of claim 3 wherein:
the gas supply line enters the first breathing channel at the proximal end and includes an entry point into the passageway of the lateral airway breathing channel lumen extending approximately two centimeters into the first breathing channel; and
the gas monitoring line enters the second breathing channel at the proximal end and extends into the second breathing channel at approximately four centimeters.

5. The oral airway of claim 1 wherein the gas supply line is an oxygen supply line.

6. The oral airway of claim 1 wherein the gas monitoring line is an end tidal carbon dioxide line.

7. The oral airway of claim 1 wherein the gas monitoring line includes a luer connector for connection to a gas monitoring device.

8. The oral airway of claim 1 further comprising a bracket affixed to the proximal end of the oral airway, the bracket securing the gas monitoring line and the gas supply line into the first and second breathing channels.

9. The oral airway of claim 1 wherein the oral airway does not require endotracheal intubation, laryngeal mask airway (LMA) placement or cuffed oral pharyngeal airway (COPA) placement.

10. The oral airway of claim 1 wherein the oral airway is useable in combination with a $O_2$/$ETCO_2$ nasal cannula.

11. The oral airway of claim 1 wherein the gas monitoring line is connected to a gas monitor providing analysis of the gases exhaled by the patient.

12. The oral airway of claim 11 wherein the gas monitoring line is connected to a carbon dioxide gas monitor.

13. The oral airway of claim 1 wherein the gas is oxygen.

14. The oral airway of claim 1 wherein the gas supply line is connectable directly to an oxygen system.

15. An oral airway system, the oral airway system comprising:
a central airway lumen having a passageway, the central airway lumen having a proximal end and an opposite distal end;
a first breathing channel positioned adjacent to the central airway lumen, the first breathing channel having a gas supply line, the gas supply line adapted to supply gas from a gas supply device to the passageway; and
a second breathing channel positioned adjacent to the central airway lumen and opposite the first breathing channel, the second breathing channel having a gas monitoring line for monitoring gases expelled from a patient, the gas monitoring line providing a conduit to monitor expelled gases within the passageway and adapted for connection to a gas monitor device;
a gas monitoring system connected to the gas monitoring line; and
a gas supply system connected to the gas supply line;
wherein the airway lumen is a unitary body having a curved extension with a partially opened portion of the oral airway for scope manipulation, the shape of the oral airway providing a patent airway for spontaneously ventilating patients undergoing moderate to deep sedation for surgical procedures, endoscopic procedures, bronchoscopic procedures, or fiber optic intubation;
wherein the airway lumen is sized and shaped to enable scope manipulation by inserting a scope through the proximal end and exiting the scope through the distal end;
whereby the airway is inserted into the mouth of the patient so that the distal end is placed in the patient's pharynx and the proximal end remains outside the mouth of the patient, the gases expelled by the patient from the second breathing channel and being sent and analyzed by the gas monitoring system and the gas supply system supplying gas through the gas supply line to the passageway of the first breathing channel and wherein the first breathing channel constantly supplies as to the patient and the second breathing channel constantly monitors expelled gases from the patient while simultaneously enabling scope manipulation through the airway lumen.

16. The oral airway system of claim 15 wherein the gas supply line is an oxygen supply line and the gas supply system supplies oxygen.

17. The oral airway system of claim 15 wherein the gas monitoring line is an end tidal carbon dioxide line and the gas monitoring system monitors and analyzes expelled carbon dioxide.

18. The oral airway system of claim 15 wherein the central airway lumen, the first breathing channel and the second breathing channel converge to a distal scoop-shaped extension.

19. An oral airway comprising:
a straight central airway lumen for manipulation of an endoscope or bronchoscope, the straight airway lumen having a distal end and a proximal end;
an airway passing through the central airway lumen;
at least one breathing channel positioned adjacent to the central airway lumen;
a bracket attached to the proximal end, the bracket securing at least one line in which a gaseous substance may flow;
wherein the line secured by the bracket enters a proximal end of a first breathing channel airway and extends into the proximal third of the airway lumen and supplies a gaseous substance to a patient; and
a second line secured by the bracket, a proximal end of a second breathing channel airway positioned opposite the first breathing channel, wherein the second line extends to the middle third of the second lateral breathing channel, the second line collecting gases exhaled by the patient;
wherein the airway lumen is a unitary body having a curved extension with a partially opened portion of the oral airway for scope manipulation, the shape of the oral airway providing a patent airway for spontaneously ventilating patients undergoing moderate to deep sedation for surgical procedures, endoscopic procedures, bronchoscopic procedures, or fiber optic intubation wherein the first breathing channel constantly supplies gas to the patient and the second breathing channel constantly monitors expelled gases from the patient while simultaneously enabling scope manipulation through the airway lumen;

wherein the airway lumen is sized and shaped to enable scope manipulation by inserting a scope through the proximal end and exiting the scope through the distal end.

* * * * *